United States Patent [19]

Tardiff, Jr. et al.

[11] Patent Number: 5,181,506
[45] Date of Patent: Jan. 26, 1993

[54] MULTILAYER PROTECTIVE GAS MASK

[75] Inventors: Albert N. Tardiff, Jr., Bel Air, Md.; Corey M. Grove, Red Lion, Pa.

[73] Assignee: The United States of America as represented by the Secretary of the Army, Washington, D.C.

[21] Appl. No.: 695,142

[22] Filed: May 2, 1991

[51] Int. Cl.$^5$ .............................................. A62B 17/04
[52] U.S. Cl. ..................... 128/201.22; 128/201.23; 128/201.29; 128/206.24
[58] Field of Search ................. 128/201.25, 205.12, 128/205.25, 205.27, 205.28, 206.12, 206.21, 206.24, 206.26, 863, 201.22, 201.29, 201.15, 201.23

[56] References Cited

U.S. PATENT DOCUMENTS

| | | | |
|---|---|---|---|
| 2,800,901 | 7/1957 | Monro | 128/201.15 |
| 2,810,386 | 10/1957 | Reed | 128/201.15 |
| 2,821,192 | 1/1958 | Monro | 128/201.15 |
| 4,296,746 | 10/1981 | Mason, Jr. et al. | 128/201.15 |
| 4,323,063 | 4/1982 | Fisichella | 128/863 |
| 4,534,344 | 8/1985 | Constance-Hughes | 128/201.15 |
| 4,764,990 | 8/1988 | Market | 128/201.15 |
| 4,881,538 | 11/1989 | Angell | 128/201.15 |
| 5,056,512 | 10/1991 | Bower et al. | 128/201.25 |

Primary Examiner—Edgar S. Burr
Assistant Examiner—Aaron J. Louis
Attorney, Agent, or Firm—Anthony T. Lane; Edward Goldberg; Michael C. Sachs

[57] ABSTRACT

A gas mask having a facepiece comprised of three separate transparent layers secured around their peripheries in a detachable manner, the inner layer being made of soft material, the middle layer being made of material that flexibly retains its form, and the outer layer being made of material for protection against liquid agents. An eye outsert is formed from the middle layer over the area around the eyes of a wearer, and a nose cone is formed from the middle layer so as to provide space about the nose and mouth. Inhaled air is drawn through channels formed in the middle layer that extend from the periphery of the facepiece to the outsert. After passing through the outsert, inhaled air passes through a channel formed in the middle layer to the nose cone. A passageway is provided for exhaled air to pass from the nose cone. Prescription lenses for the wearer are integrally formed in a member that can be snapped into the eye outsert. Seals are provided around the periphery of the facepiece and around the nose cone by channels in the middle layers that are filled with a gel and/or compressed air. A hood of treated elastic material fits over the head of the wearer so as to draw the seals into contact with the wearer's skin. The hood surrounds the neck and has a flap that overlies the chest of the wearer, and an air pump and decontamination cannister coupled to the channels for inhaled air are mounted in the flap. Electronic controls are also mounted on the flap for controlling the pump so as to maintain a constant pressure between inhaled and exhaled air.

22 Claims, 4 Drawing Sheets 5,181,506

MULTILAYER PROTECTIVE GAS MASK

GOVERNMENT INTEREST

The invention described herein may be manufactured, used, and licensed by or for the Government for governmental purposes without the payment to us of any royalty thereon.

FIELD OF THE INVENTION

This invention is in the field of protective gas masks primarily designed for use by military personnel.

BACKGROUND OF THE INVENTION

Gas masks have been used by the military since the beginning of World War I. Whereas they perform the basic function of protecting the wearer from gas and liquid agents, they have the following deficiencies.

Protection System: The present masks cover the face with butyl coated nylon which offers only six hours of liquid agent protection.

Decontamination: After a given exposure to contaminating gas, the entire mask has to be cleaned and there are limited provisions for hasty cleaning.

Recognition: Because the only transparent portion is in a small area about each eye, it is difficult to recognize the wearer by sight.

Field of View: The field of view is limited because the wearer's lenses contained in the mask are too far from the eyes, and it is extremely difficult for the wearer to look down.

Use With Weapon: The design of the optics of present weapons requires that the distance between the pupil of the operator's eye and the eyepiece of the weapon, which is termed eye relief, be 25 mm or less, but the eye relief for present masks is greater than this. Furthermore, the gas filter cannister and the hoses between it and the mask drastically interfere with the use of many weapons.

Optical Correction: In present masks, separate lenses ground to the wearer's prescription are mounted within the mask at a distance that is too far from the eye for best vision, and the lenses are too small.

Laser Protection: Protection against laser beams is provided by a specially coated outsert that is mounted in front of the correction lenses so as to further increase the eye relief.

Communication: The intelligibility of spoken words is far below that required for adequate communications.

Breathing Resistance: The resistance to inhaling is larger than desired primarily because of the construction of the filter cannister, but the necessary one way flapper exhalation valve also provides too much resistance.

Comfort: The buckles for retaining the mask on the head of the wearer become uncomfortable after a few hours so that the wearer often removes the mask before it is safe to do so.

Heat Burden: The face piece of the mask is comprised of impermeable materials and is not ventilated so that intolerable heat stress situations build up quickly in warm ambient temperatures.

Physical protection: Although limited protection is provided against the elements and branches, there is little or no protection against flying fragments.

Thus the state of the art gas masks are unsatisfactory in nearly every required function. They provide protection for too short a time, are difficult to decontaminate and are optically incompatible with weapons. In addition, it is difficult for one wearer to recognize or talk clearly to another. Furthermore, because of breathing resistance and heat buildup, the masks may be discarded before it is safe to do so.

BRIEF DESCRIPTION OF AN EMBODIMENT OF THE INVENTION

In one embodiment of the invention, the face piece of the mask is comprised of three separate layers of transparent material. The inner layer is made of soft material so as to form a comfortable seal when pressed against the skin; the middle layer is flexible but retains its shape, and the outer layer is made of material for protection against liquid agents. The outer layer is detachably secured to the middle layer at points around its periphery so that it can be removed for hasty or thorough cleaning. Alternatively, the outer layer can be disposed of and another layer can be quickly substituted for it without removal of the entire mask. The inner layer can be detachably or permanently secured to the middle layer.

A nose cone that covers the nose, mouth and chin is formed with the middle layer and is sealed from the rest of the face piece. A seal is also formed around the periphery of the face piece.

An outsert surrounding the eyes and extending over the bridge of the nose is formed from the middle layer, and prescription lenses for the wearer are integrally formed on a single piece that snaps into the inside of the outsert. A cup formed from material resistant to liquid agents and having an inner layer of laser protective coating is removably mounted on the outside of the outsert.

In a preferred embodiment, the seals around the periphery of the face piece and around the nose cone are provided by inwardly facing channels formed in the middle layer that are heat sealed or otherwise attached along their edges to the inner layer. The channels are filled with means for forming an inwardly extending bulge in the inner layer. The bulge forms a very good seal against contaminants when it is pressed against the skin of the wearer by tension supplied by a treated elastic cloth hood that fits tightly over the head. The hood also extends around the neck and has aa skirt extending over the upper chest and shoulders.

Passageways for air being inhaled pass from the periphery of the face piece to the outsert around the eyes and from the outsert to the nose cone. One way flapper valves are inserted in one of the passageways to prevent the passage of exhaled air. The passageways are preferably formed by inwardly facing channels in the middle layer that are attached to the inner layer along their edges.

Passageways for exhaled air can be formed in the same manner as the passageways for inhaled air. The ends of the channels forming them are in communication with the interior of the nose cone and extend to the periphery of the face piece. Alternatively, exhaled air can pass through a separate tube or tubes passing between the skin of a wearer and the seal around the periphery of the face piece. A one way flapper valve is provided to prevent air from being inhaled through the passageways for exhaled air.

Purification of inhaled air is achieved by connecting the passageways for inhaled air to a filter containing activated charcoal or other such substance. In order that the filter have as little effect as possible on the movement of the wearer and his ability to operate weapons, the filter is made large and flat and is mounted in the skirt of the hood covering the upper chest.

Reduction of resistance to breathing is achieved by connecting an air pump to the filter. The pump can be controlled manually or by electronics also mounted in the skirt of the hood that maintain a given differential between inhaled and exhaled air.

Protection from flying debris is provided by a Lexan ® mask that is pivoted at two opposite points on the face piece so that it can be positioned over the head or swung down so as to cover the entire face piece.

Because there is no large structure such as an elephant trunk-like cannister mounted in front of the mouth, the wearer's spoken word can be easily understood. Furthermore, his lips can be seen. For electrical communication, a microphone is mounted inside the nose cone, and the leads therefore are run between the skin of the wearer and the seal around the periphery of the face piece.

Since the seals formed by the bulges in the inner layer space the relatively stiff middle layer of the face piece from the wearer's head, cooling and drying air can be forced between the skin and the thin inner layer if desired.

BRIEF DESCRIPTION OF THE DRAWINGS

Various embodiments of the invention are described below with reference to the drawings, in which like items are indicated by the same reference numbers, wherein:

FIG. 3A is a cross-section of a snap used in attaching outer and inner layers to the middle layer of a face piece.

DETAILED DESCRIPTION OF THE INVENTION

Figure 1:
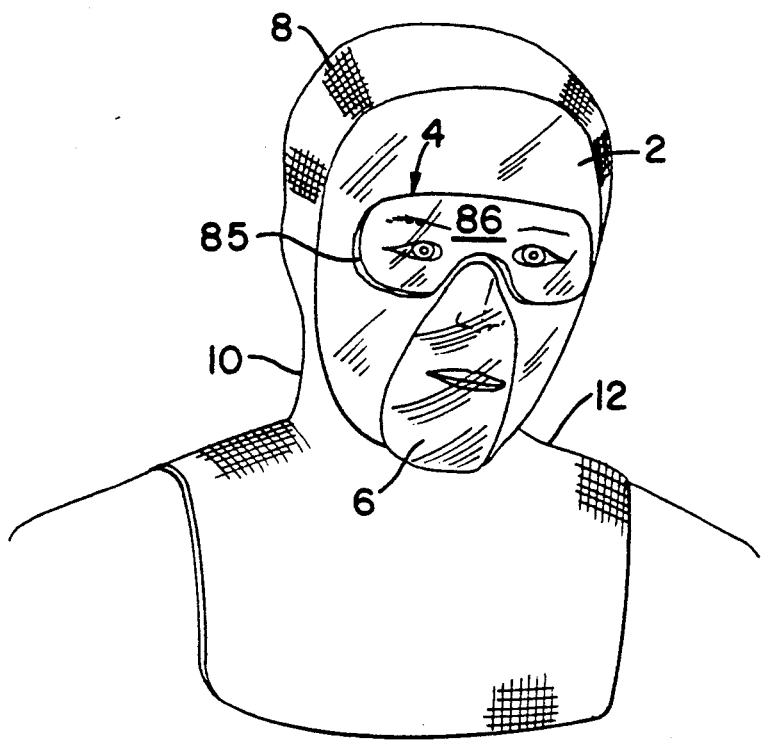
FIG. 1 is a frontal pictorial view of a person wearing a mask of this invention.
Figure 2:
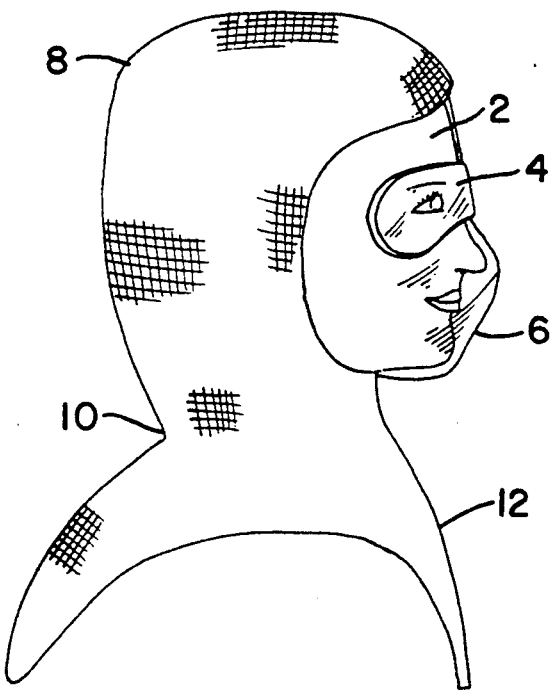
FIG. 2 is a pictorial side view of a person wearing the mask of this invention.

FIG. 1 is a frontal pictorial view of a person wearing a mask of this invention. A transparent face piece 2 is shown as having an eye outsert 4, a nose cone 6 and a hood 8 of knitted elastic material that is joined to the periphery of the face piece 2. The hood 8 has a section 10 surrounding the neck and a skirt 12 that drapes over the upper chest. In order to protect the head from liquid agents, the hood 8 is treated with latex or a fluropolymer. It is desirable that the hood 8 have a tight fit in order to draw the face piece 2 firmly against the head and thereby form a seal around its periphery in a manner to be explained. FIG. 2 shows the elements of FIG. 1 as they appear in a pictorial side view.

Figure 3:
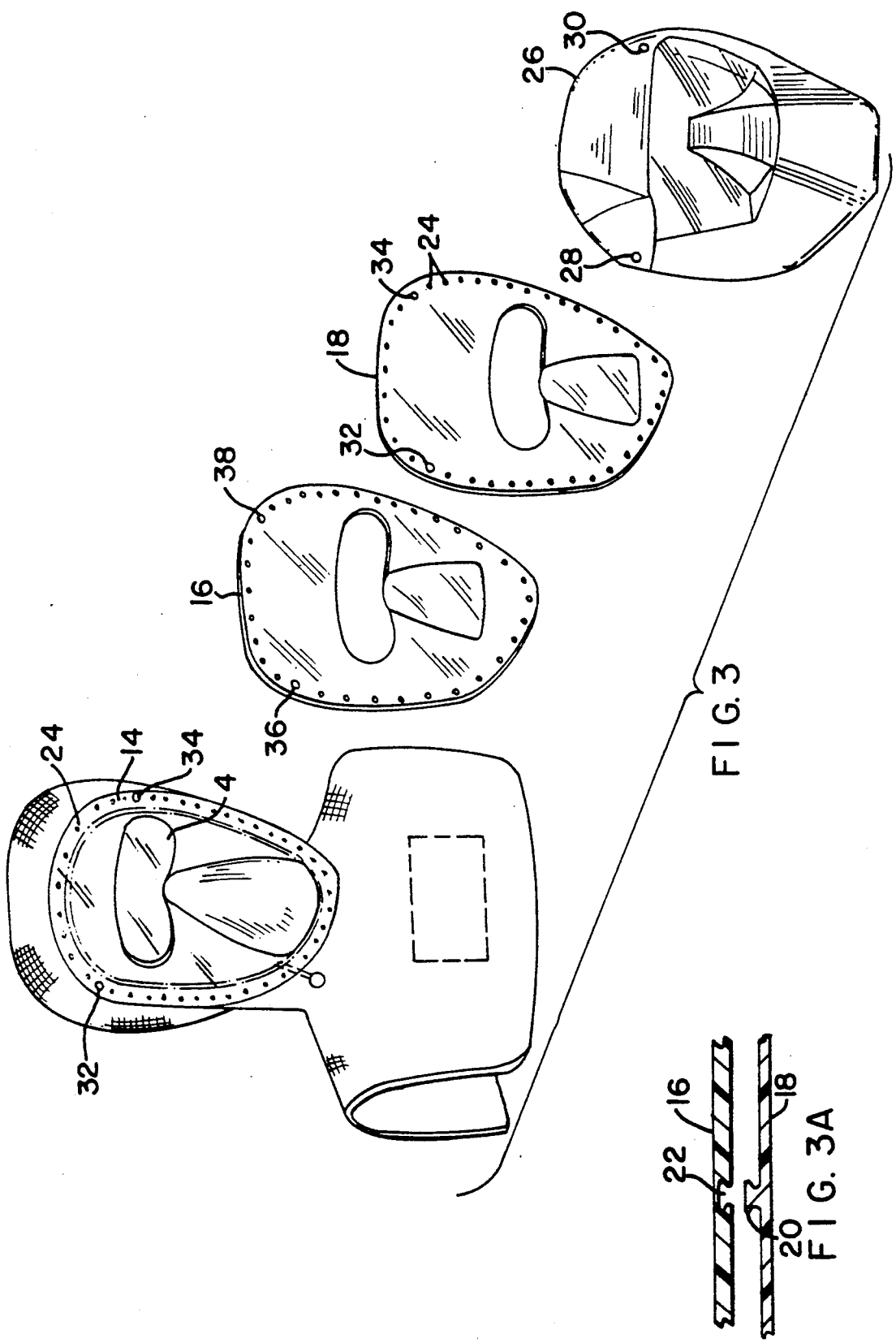
FIG. 3 is an exploded view of the face piece of the mask of this invention.

FIG. 3 is an exploded view of the three layers forming the face piece 2. The inner layer 14 is made of a soft material such as KRATON ® that is comfortable when pressed against the skin. The relatively thick middle layer 16 is made of material such as urethane which, while yielding, will retain the shape of the outsert 4 and the nose cone 6. The outer layer 18 is selected for its ability to provide protection against liquid agents such as mustard gas. Fluropolymers are suitable for this purpose.

In this particular embodiment, the inner layer 14 and the outer layer 18 are attached to the middle layer 16 at points around their respective peripheries. One way of making such an attachment is shown in FIG. 3A, wherein the layer 18 is shown having a bulbous projection 20 that snaps into a similarly shaped cavity 22 in the middle layer 16. The inner layer 14 is attached to the middle layer 16 in the same manner. The points of attachment of the outer layer 18 to the middle layer 16 are indicated by the dots 24, and the points of attachment of the inner layer 14 to the middle layer 16 are indicated by the dots 25. It is preferable that the points 24 be interleaved with the points 25.

A distinct advantage of the mask of this invention is that the outer layer 18 can be easily removed, quickly washed and reattached. Alternatively, it could be replaced by a similar layer that has been thoroughly cleaned, or a new such layer.

Another advantage of the mask of this invention is that considerable protection against flying debris can be provided by a transparent face piece cover 26, shown in FIG. 3, that is made of an impact resistant material like LEXAN ®. The cover 26 can be carried separately or on the back or top of the head and attached to the face piece 14, 16, 18 by projections like 20 of FIG. 3A that can be passed through the outer layer 18 and snapped into cavities like 22 of FIG. 3A in the middle layer 16. For example, the projections could be located at points 28 and 30 on the cover 26, extend through openings 32 and 34, respectively, in the outer layer 18, and into cavities 36 and 38 in the middle layer 16.

Figure 4:
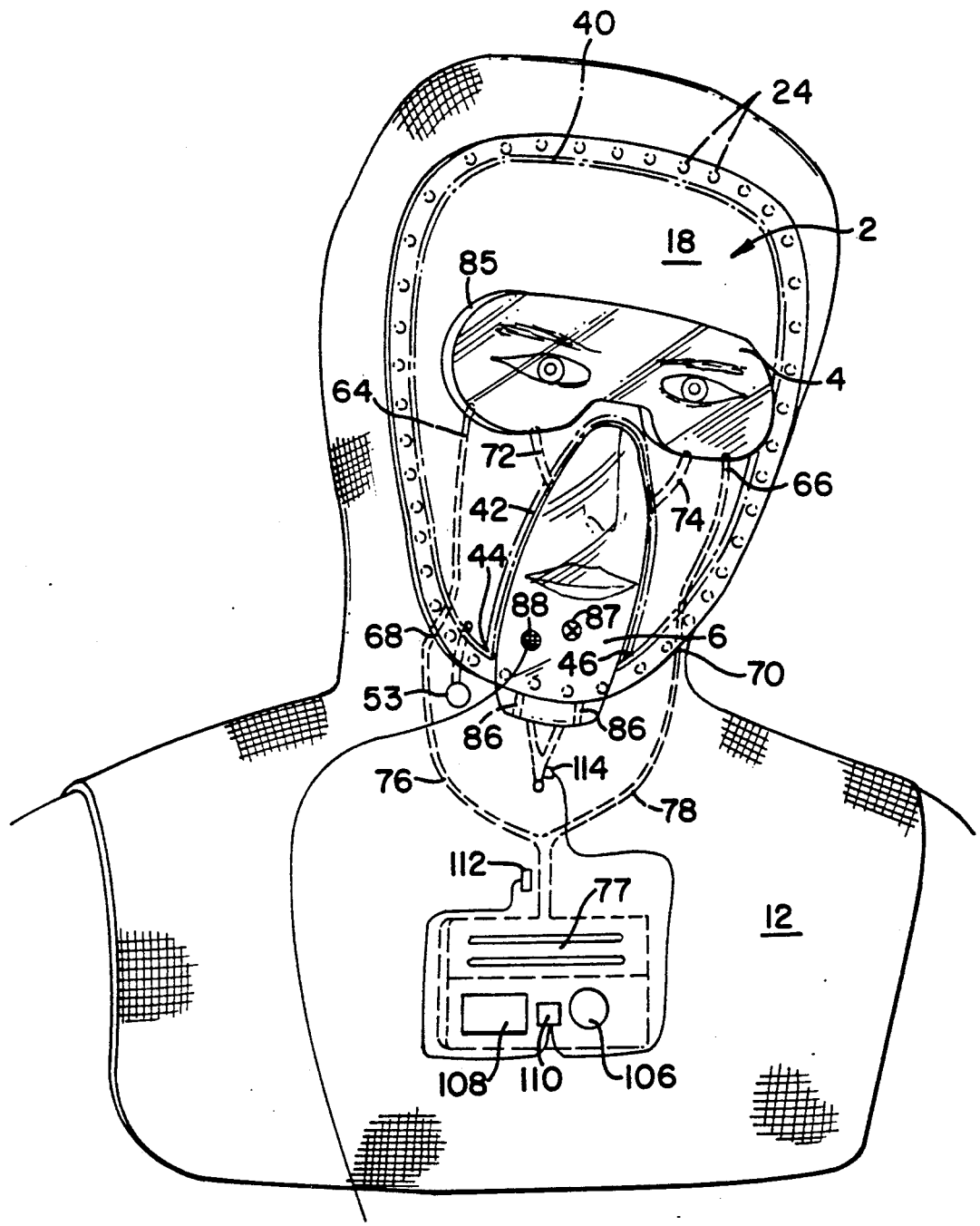
FIG. 4 is a front view of a person wearing the mask of this invention in which the seals and breathing passageways are shown by broken lines.

Reference is now made to FIG. 4 for a description of the locations of seals. As shown by the dashed or broken lines 40, a seal is formed around the periphery of the face piece 2 that is just inside the points 24 of attachment of the outer layer 18. In this frontal view, the seal 40 passes out of view when it passes under the wearer's chin. A seal around the nose cone 6 is shown by dashed lines 42 that pass over the bridge of the nose cone 6 and along either side of it so as to intersect the seal 40 of the face piece at points 44 and 46.

Figure 5:
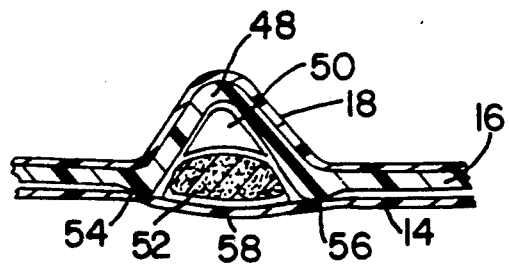
FIG. 5 is a cross-sectional view of one form of seal used in this invention.

Although the seals 40 and 42 can be formed in different ways, FIG. 5 illustrates a seal constructed in accordance with one aspect of this invention. An inwardly facing channel 48 having a cross section as shown is formed in the middle layer 16. A tube 50 containing compressed air is placed in the bottom of the channel 48, and a tube 52 containing a soft gel is placed on top of it. Alternatively, air can be manually pumped into the tube 50 by a "button" pump 53 shown in FIG. 4 that is similar to that used to inflate sneakers. Heat or adhesive is used to adhere the sides 54 and 56 of the channel 48 to the inner layer 14. Compressed air in the tube 50 pushes against the tube 52 and produces a bulge 58 in the inner layer 14 that forms a seal with the wearer's skin when drawn against it by the hood 8. Alternatively, the tube 52 of gel can be eliminated and the bulge formed by air in the tube 50. The bulge makes it possible to introduce cooling or drying air between the skin and the inner layer 14. Although the seals 40 and 42 could be entirely separate, their junctions at 44 and 46 permit them to receive air from the same pump.

Figure 6:
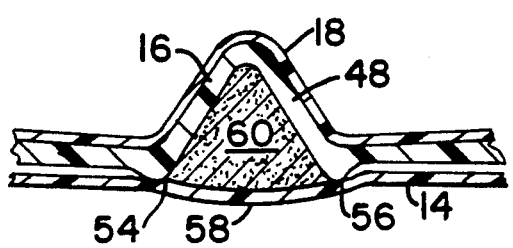
FIG. 6 is a cross-sectional view of another form of seal used in this invention.

Another way to form a seal in accordance with this invention is shown in FIG. 6. No air tube is used and the channel 48 is overfilled with a soft get 60 so as to produce a bulge 58, when the edges 54 and 56 of the channel 48 are adhered to the inner layer 14. Alternatively, the gel could be contained in a tube, not shown, that overfills the channel 48.

Reference is again made to FIG. 4 for the location of breathing passageways for the mask. Instead of using a large single air intake tube that gets in the way, relatively flat passageways 64 and 66 are used that are formed between the inner and middle layers 14 and 16 of the face piece in a manner to be explained. The passageway 64 engages the periphery of the face piece 2 at a point 68, passes through the seal 40 and into the eye outsert 4. The passageway 66 engages the periphery of the face piece 2 at 70 and enters the eye outsert 4 on the other side. Air passageways 72 and 74 respectively couple inner points of the eye outsert 4 to the nose cone 6. Tubes 76 and 78 respectively couple the air intake passageways 64 and 66 to a cannister or filter 77 of activated charcoal. Thus, when the user inhales, air is drawn through the cannister 77, the tubes 76 and 78, the passageways 64 and 66, the eye outsert 4 and the passageways 72 and 74.

Figure 7:
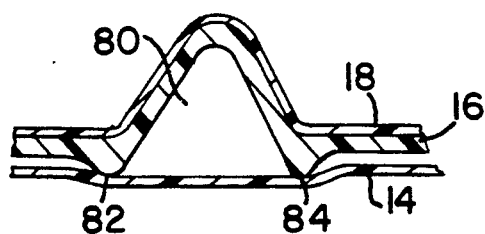
FIG. 7 is a cross-sectional view of a breathing air passageway used in this invention.

FIG. 7 illustrates how the air passageways 64, 66, 72 and 74 are constructed in accordance with an aspect of this invention. An inwardly facing channel 80 is formed via the middle layer 16, and its edges 82 and 84 are adhered by heat or glue to the inner layer 14 so as to form a passageway through which air can pass.

Figure 8:
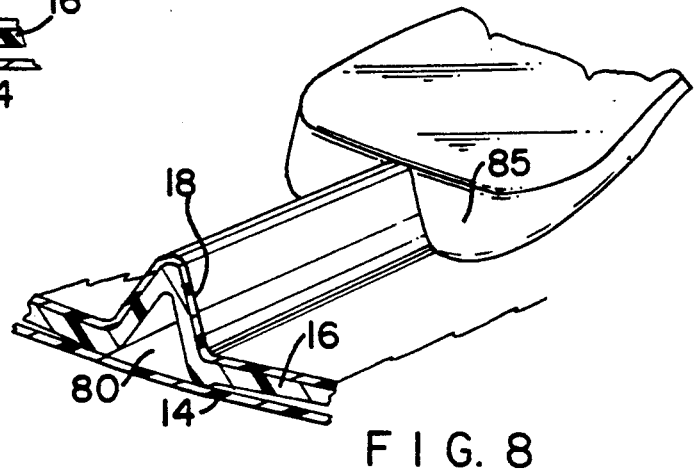
FIG. 8 illustrates in partial cross-section the junction of an air passageway and the eye outsert for a mask of this invention.

FIG. 8 illustrates the manner in which the air passageway 82 enters the interior of the eye outsert 4 by passing through its peripheral wall 85.

Exhaled air can pass through passageways to the nose cone 6 that are constructed as the passageways 64, 66, 72 and 74, or tubes 86 can be inserted into the nose cone by passing them under the seal at the periphery of the face piece. Alternatively, a one way valve 87 can be mounted in the nose cone.

Audio communication through the nose cone 6 of the face piece 2 is clearly understandable because the layers 14, 16 and 18 are so thin and the wearer's lips can be seen. Electronic communication can be provided in the usual way by mounting a microphone in the nose cone 6.

Figure 9:
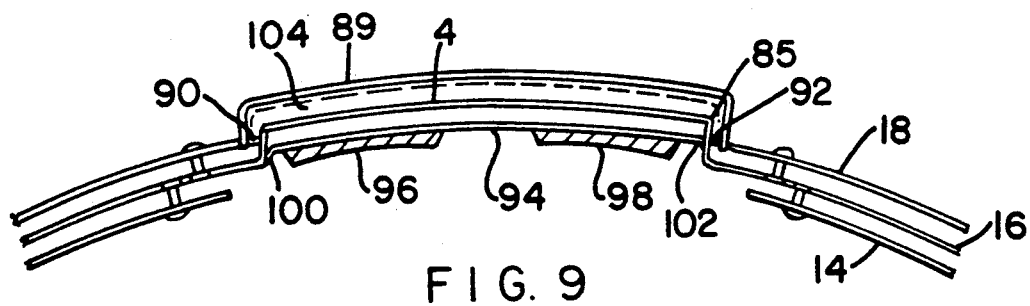
FIG. 9 is a cross-section of the eye region of a mask of this invention in which the eye outsert and the protective cup over the eye outsert are shown in detail.

Reference is now made to FIG. 9 for a more detailed description of the eye outsert 4 and other components mounted on it. A protective cup 89 that may be made of impact resistant material like LEXAN ® is snapped onto the wall 85 of the outsert 4 at convenient points such as 90 and 92 by means such as shown in FIG. 3A. A lens member 94 having the wearer's prescription lenses 96 and 98 integrally formed therewith is snapped to convenient point such as 100 and 102 to the wall 85 by means such as shown in FIG. 3A. Protection against laser beams is provided by a suitable coating 104 on the inside of the protective cup 89.

As shown, there are spaces between the cup 89, the outsert 4 and the lens member 94, but the juxtaposed surfaces all have the same shape so as to reduce the overall thickness when pressed together. The outer surface of the protective cups 89 is 0.25 mm from the pupil of the eye, in this example.

In order to reduce the resistance to inhaled air an electrically driven pump 106, powered by a battery 108, is mounted in the skirt 12 and coupled to the cannister 77. The pump 106 can be manually controlled or it can operate under the control of electronic circuits 110 to maintain a constant differential between the air pressure in the air intake tubes 76 and 78 that is indicated by a transducer 112, and the air pressure in the air exhaust tube 86 that is indicated by a transducer 114.

Although various embodiments of the invention have been shown and described herein for purposes of illustration, they are not meant to be limiting. Those of skill in the art may recognize certain modifications to the various embodiments of the invention, which modifications are meant to be covered by the spirit and scope of the amended claims.

What is claimed is:

1. A gas mask comprising:
   a face piece having a plurality of layers, the outer layer being removably attached to an adjacent layer;
   a nose cone formed in said face piece for providing an enclosed space about the nose and mouth of wearer;
   an eye outsert formed from one of said layers;
   means forming inhaled air passageways between adjacent layers from the periphery of said face piece to said eye outsert and from said eye outsert to said nose cone:
   means defining an exhaled air passageway for conducting air from said nose cone to a point outside of said mask;
   means around the periphery of said face piece for forming a seal with the head of a user when pressed thereagainst;
   means for forming a seal between the periphery of said nose cone and the skin of a user when pressed thereagainst; and
   means adapted to pull the face piece toward the head of a wearer so as to press said seals against the head of a wearer.

2. A gas mask as set forth in claim 1, wherein said face piece has three layers that are removably attached at their peripheries.

3. A gas mask as set forth in claim 2, wherein said three layers include an inner layer made of soft material, a middle layer made of material that can hold its shape at normal ambient temperatures, and an outer layer made of material for liquid agent protection.

4. A gas mask as set forth in claim 3, wherein said inner layer is made of KRATON ®, said middle layer is made of urethane, and said outer layer is made of a fluropolymer.

5. A gas mask as set forth in claim 3, wherein said eye outsert is formed from said middle layer.

6. A gas mask as set forth in claim 5, wherein a cup made of impact resistant material is removably attached to and covers said eye outsert.

7. A gas mask as set forth in claim 6, wherein said cup includes means for protecting eyes from laser radiation.

8. A gas mask as set forth in claim 5, wherein means are provided in said outsert for mounting optical correction lenses for the wearer.

9. A gas mask as set forth in claim 3, wherein each seal is comprised of:
   a channel formed in said middle layer having edges adjacent said inner layer;
   means for bonding said edges to said inner layer at least at a plurality of points therealong; and
   means contained in said channel for forming a bulge in said inner layer.

10. A gas mask as set forth in claim 9, wherein said means for forming a bulge in said inner layer is pressurized gas in said channels.

11. A gas mask as set forth in claim 10, wherein a gas pressure pump mounted on said mask is coupled to said channel.

12. A gas mask as set forth in claim 9, wherein said means for forming a bulge in said inner layer includes gel under pressure.

13. A gas mask as set forth in claim 9, wherein said means for forming a bulge in said inner layer includes a tube containing gel.

14. A gas mask as set forth in claim 9, wherein said means for forming a bulge in said inner layer is comprised of:
   a first tube mounted in the bottom of said channel; and
   a second tube containing gel mounted between said first tube and said inner layer.

15. A gas mask as set forth in claim 14, wherein a pump mounted on said mask provides pressure to the gas in said first tube.

16. A gas mask as set forth in claim 14, wherein said first tube contains gas under pressure.

17. A gas mask as set forth in claim 3, wherein said inhaled air passageways comprise:
   a channel formed in said middle layer having edges adjacent said inner layer; and
   means sealing said edges of said channel to said inner layer.

18. A gas mask as set forth in claim 1, wherein said means adapted to pull the face piece toward the head of a wearer so to press said seals against the head of a wearer comprises:
   a hood of elastic material attached to the periphery of said face piece that stretches when placed over the head and around the neck of a wearer.

19. A gas mask as set forth in claim 18, further comprising an extension of said hood adapted to drape over the chest of a wearer.

20. A gas mask as set forth in claim 19, further comprising:
   a decontamination cannister mounted on said extension of said hood, the dimensions of said cannister parallel to the chest of a wearer being greater than its dimension perpendicular to the chest of a wearer; and
   means coupling said cannister to said inhaled air passageways.

21. A gas mask as set forth in claim 20, further comprising:
   an air pump coupled so as to force air through said cannister and said inhaled air passageways.

22. A gas mask as set forth in claim 21, further comprising:
   means for providing a signal indicative of the pressure in said inhaled air passageways;
   means for providing a signal indicative of the pressure in said exhaled air passageway; and
   electronic means responsive to said signals for controlling said pump so as to tend to maintain a constant difference between said pressures.

* * * * *